United States Patent
Yoshime Watanabe

(10) Patent No.: US 10,743,974 B2
(45) Date of Patent: Aug. 18, 2020

(54) FOLLICULAR ASPIRATION NEEDLE

(71) Applicant: Osnir Yoshime Watanabe, Cravinhos (BR)

(72) Inventor: Osnir Yoshime Watanabe, Cravinhos (BR)

(*) Notice: Subject to any disclaimer, the term of this patent is extended or adjusted under 35 U.S.C. 154(b) by 290 days.

(21) Appl. No.: 15/739,357

(22) PCT Filed: Jun. 24, 2016

(86) PCT No.: PCT/BR2016/050146
§ 371 (c)(1),
(2) Date: Jan. 23, 2018

(87) PCT Pub. No.: WO2016/205914
PCT Pub. Date: Dec. 29, 2016

(65) Prior Publication Data
US 2018/0193123 A1    Jul. 12, 2018

(30) Foreign Application Priority Data
Jun. 24, 2015 (BR) .............................. 202015015333

(51) Int. Cl.
*A61D 19/04* (2006.01)
*A61M 5/34* (2006.01)
(Continued)

(52) U.S. Cl.
CPC ............ *A61D 19/04* (2013.01); *A61B 17/435* (2013.01); *A61M 1/008* (2013.01);
(Continued)

(58) Field of Classification Search
CPC ........ A61D 19/00; A61D 1/10; A61B 17/425; A61B 17/43; A61B 17/435; A61B 17/46
See application file for complete search history.

(56) References Cited

U.S. PATENT DOCUMENTS 4,299,217 A * 11/1981 Sagae ................. A61M 5/1582
604/167.01
5,545,152 A * 8/1996 Funderburk .......... A61M 39/14
604/535

(Continued)

FOREIGN PATENT DOCUMENTS

| BR | PI0605094   | 6/2008  |
|----|-------------|---------|
| JP | 2004-329923 | 11/2004 |
| JP | 2006-055219 | 3/2006  |

OTHER PUBLICATIONS

Darwin Microfluids needle gauge table. 4 pages. Vincent Rocher. (Year: 2019).*

(Continued)

*Primary Examiner* — Samuel G Gilbert
(74) *Attorney, Agent, or Firm* — Sheridan Ross PC

(57) ABSTRACT

The invention refers to a needle for follicular aspiration, having a base with a through-hole, inside of which a needle cannula is coupled, the needle cannula having a front aspiration end which protrudes from a front end of the base, and a rear end which freely protrudes from the rear end of the base, the through-hole of the base having a frustroconical segment tapering from the rear end towards the front end of the base, forming a gap between the inner surface of the base and the outer surface of the needle cannula for coupling a biological sample collecting line.

19 Claims, 6 Drawing Sheets

Figure 1:
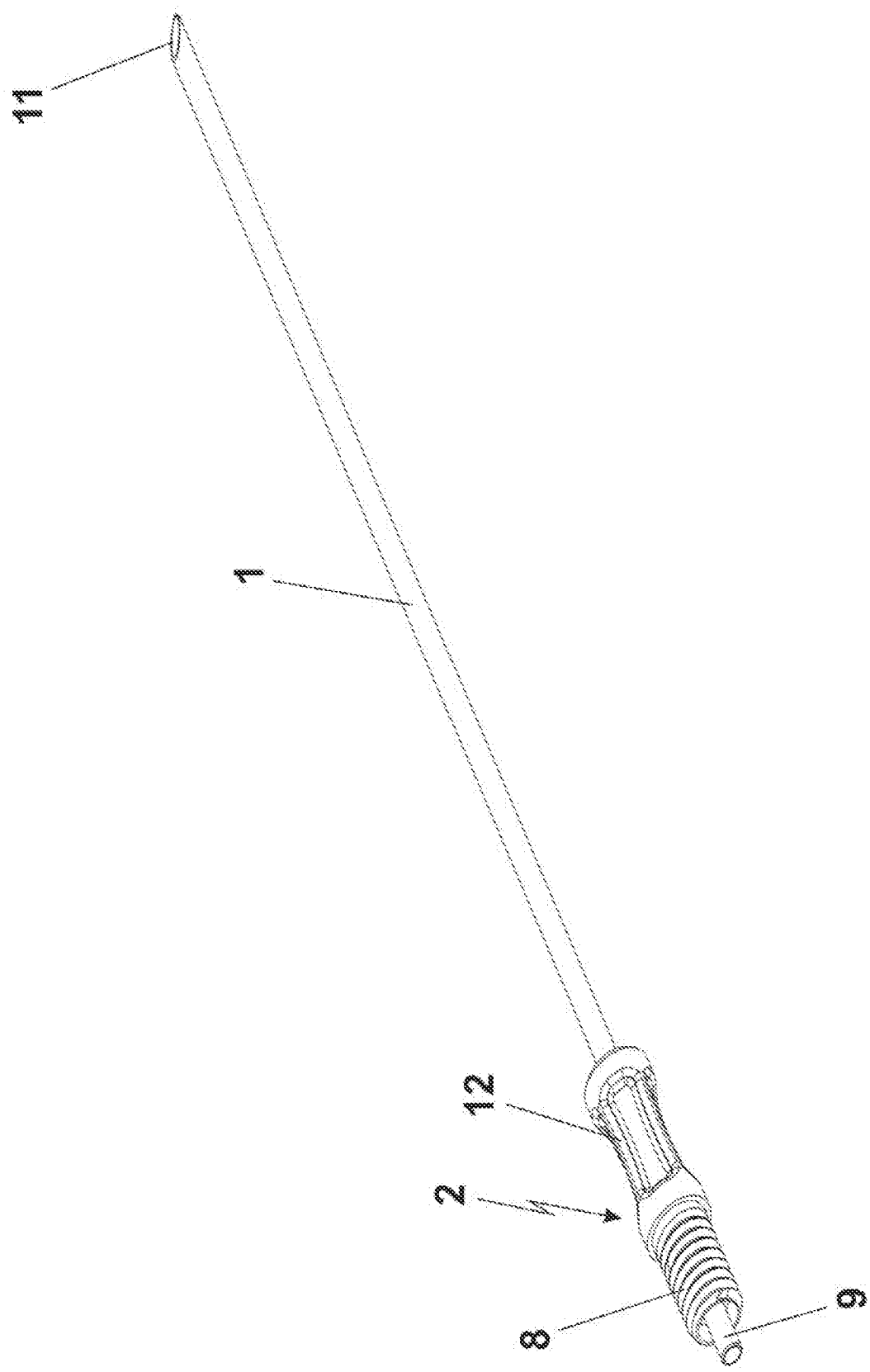

(51) Int. Cl.
    *A61M 5/32*     (2006.01)
    *A61M 1/00*     (2006.01)
    *A61B 17/435*   (2006.01)

(52) U.S. Cl.
    CPC ............ *A61M 5/3293* (2013.01); *A61M 5/34* (2013.01); *A61M 5/343* (2013.01); *A61M 5/346* (2013.01)

(56) References Cited

U.S. PATENT DOCUMENTS

| | | | | |
|---|---|---|---|---|
| 7,736,337 B2 * | 6/2010 | Diep | ................ | A61M 25/0097 604/164.01 |
| 8,708,376 B2 * | 4/2014 | Tracey | ............... | A61M 39/1011 285/332 |

OTHER PUBLICATIONS

International Search Report prepared by the Instituto Nacional Da Propriedade Industrial for International Application No. PCT/BR2016/050146, dated Aug. 8, 2016.

* cited by examiner

FOLLICULAR ASPIRATION NEEDLE

CROSS REFERENCE TO RELATED APPLICATIONS

This application is a national stage application under 35 U.S.C. 371 and claims the benefit of PCT Application No. PCT/BR2016/050146 having an international filing date of 24 June 2016, which designated the United States, which PCT application claimed the benefit of Brazil Patent Application No. BR202015015333-9 filed 24 June 2015, the disclosures of each of which are incorporated herein by reference in their entirety.

The present utility model patent relates to a new shape and arrangement introduced to a needle for follicular aspiration, pertaining to the veterinary technical sector, in particular, it is a needle for follicular aspiration of oocytes in animals. The needle for follicular aspiration of the present application enables easy coupling to the rest of the follicular aspiration equipment, such that it is possible to obtain practical, safe and functionally advantageous results.

Normally, the aspiration of oocytes is carried out with the assistance of an aspiration guide device, which has an orifice where the needle is introduced. The needle disposed in the aspiration guide device is also connected to a vacuum pump through a tube for the passage of the biological sample, also referred to as line, enabling the suction of said material. An ultrasound probe is also coupled to the aspiration guide device, to enable visualization of the oocyte and the uterine cavity where the needle is inserted. The ovarian follicles are thus visualized by means of ultrasound and are harvested by the needle, passing through the line to a collector tube.

Two types of needles are known on the market for carrying out the process of follicular aspiration: the conventional needle and the long needle. The conventional needle has a large base diameter, such that the orifice of the aspiration guide device also needs to be larger. The main drawback of the conventional needle is the difficulty in assembling: since the needle is short, it is necessary to use a mandrill (elongating rod), which will be responsible for leading the needle into the guide device which will be introduced into the animal.

Thus, to fasten the needle to the mandrill, an intermediary part is used, which is also used to fasten and seal the line with the needle. The use of this intermediary part makes the assembly process more laborious, as well as time-consuming, whereby increasing the chances of contamination, since the place where the collection and equipment assembly is carried out does not always have ideal aseptic conditions.

The second type of known needle, the long needle, presents a longer cannula, so the use of a mandrill is no longer necessary. However, fastening the line at its base is not a practical process, its cost is higher and the aggression to the environment is greater, since needles are disposable.

Additionally, when it is necessary to apply force on the needle at the moment of insertion and material collection, there is a possibility of damage to the ovary of the animal, especially those subject to aspiration several times, and it may also rupture the follicle.

Another problem with long needles is their adaptation to the various types of aspiration guide devices available on the market and the sealing of all the attached components, to prevent loss of the biological sample. In most devices, fastening the needle into the orifice of the guide device can only be achieved by using a mandrill, and involves coupling three or more different components, especially when there is a difference in the diameter of the line, the guide device and the needle, which requires the coupling of various additional adaptation and sealing parts in order to guarantee stable and seal-tight fastening between all the components.

Therefore, the objective of the aspiration needle that is the object of this utility model is to enable faster, seal-tight and efficient coupling of the combination of needle, line and guide device, preventing loss of biological sample, trauma to the animal and possible contamination, whereby solving the drawbacks referred to above, and to provide other advantages deriving from the conception thereof.

Figure 2:
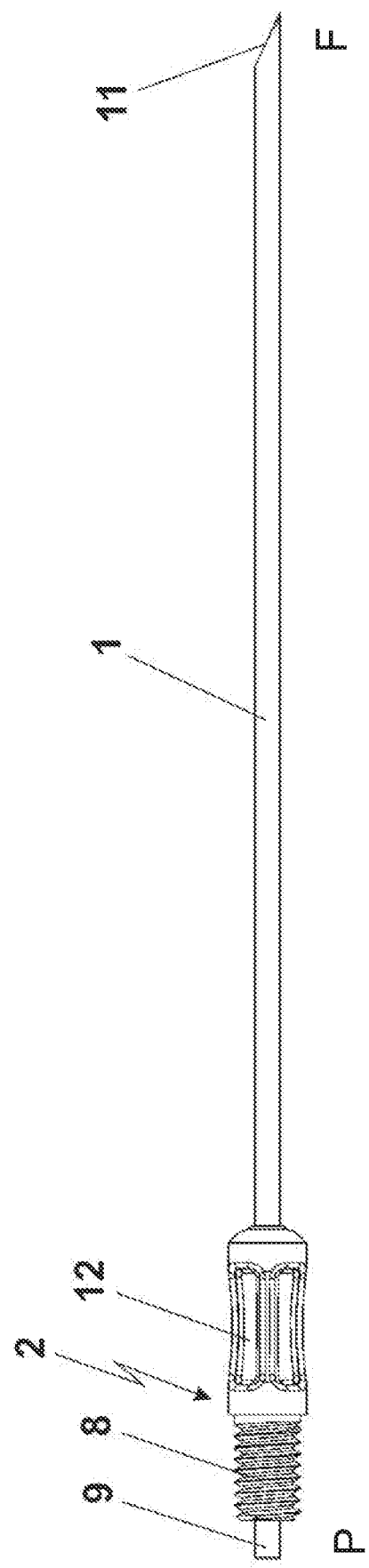
Figure 3:
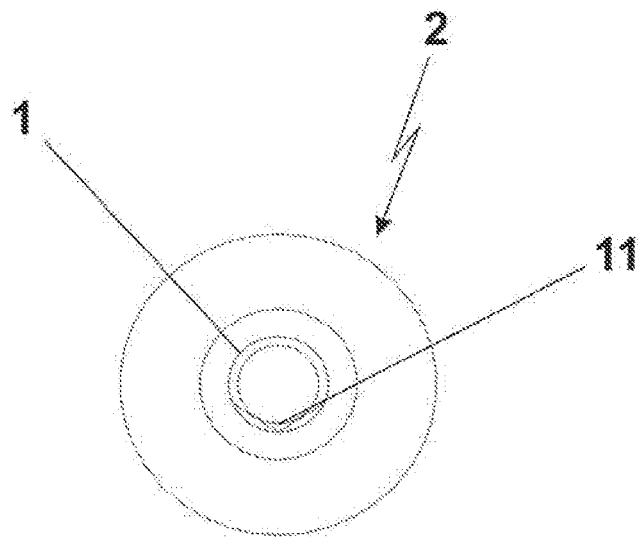
Figure 4:
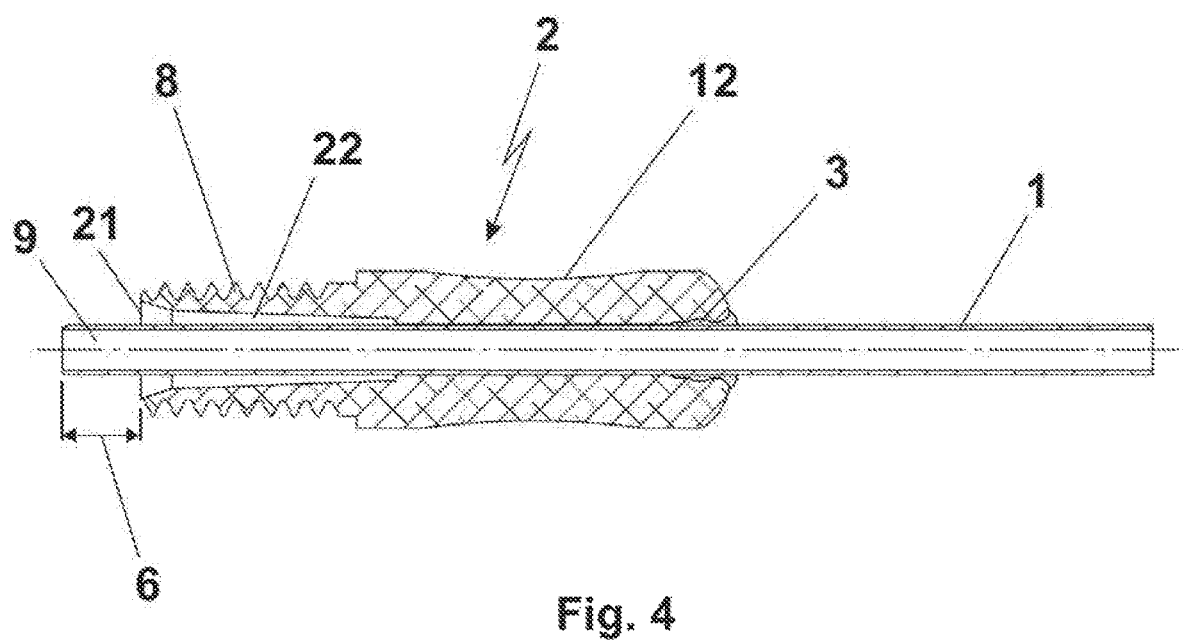
Figure 5:
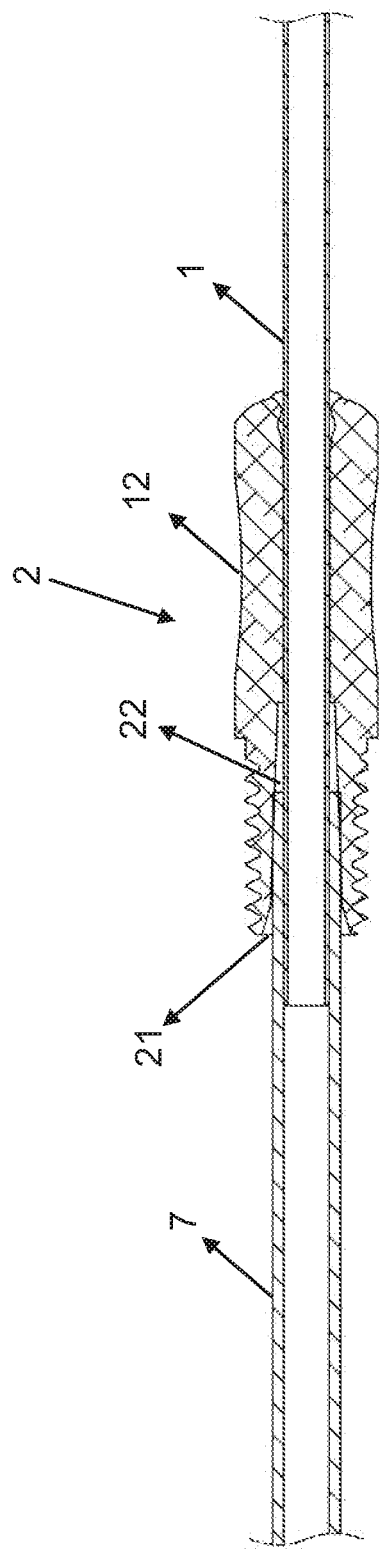
Figure 6:
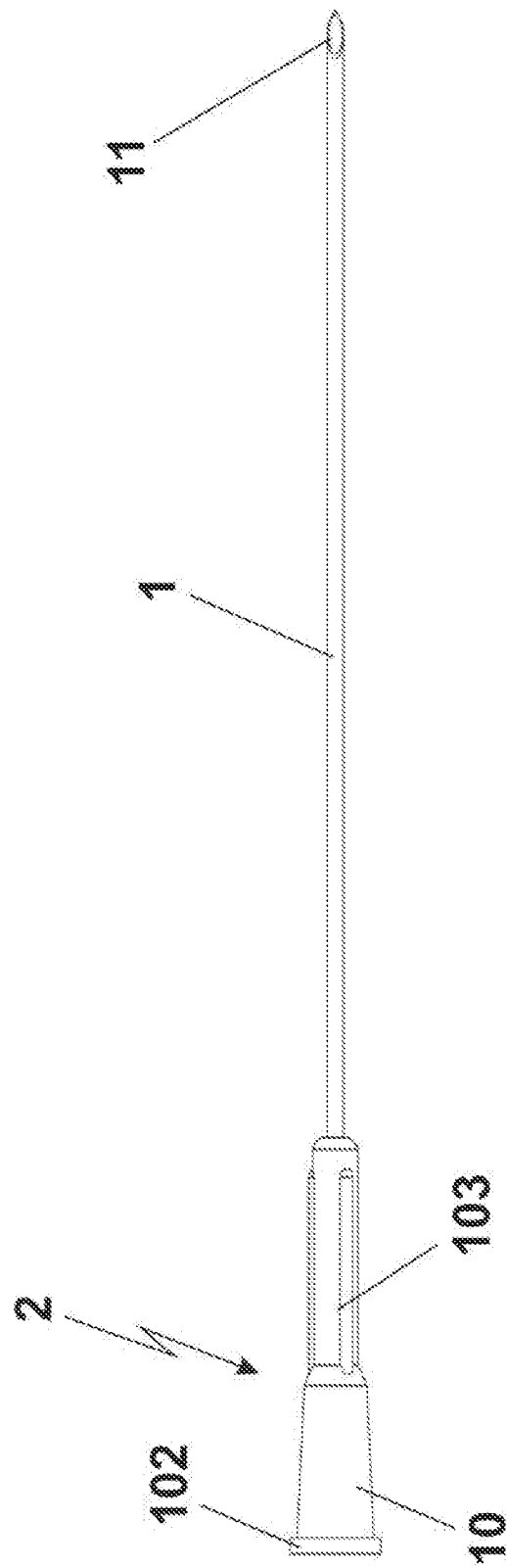

The follicular aspiration needle will be better understood by way of the accompanying drawings, which schematically represent:

FIG. 1—a perspective view of the first embodiment of the follicular needle of the present invention;

FIG. 2—a side view of the first embodiment of the follicular needle;

FIG. 3—an expanded front view of the first embodiment of the follicular needle;

FIG. 4—a cross-sectional side view of the rear part of the first embodiment of the follicular needle;

FIG. 5—a cross-sectional side view of the rear part of the first embodiment of the follicular needle coupled to the line of the system;

FIG. 6—a side view of a second embodiment of the follicular needle; and

Figure 7:
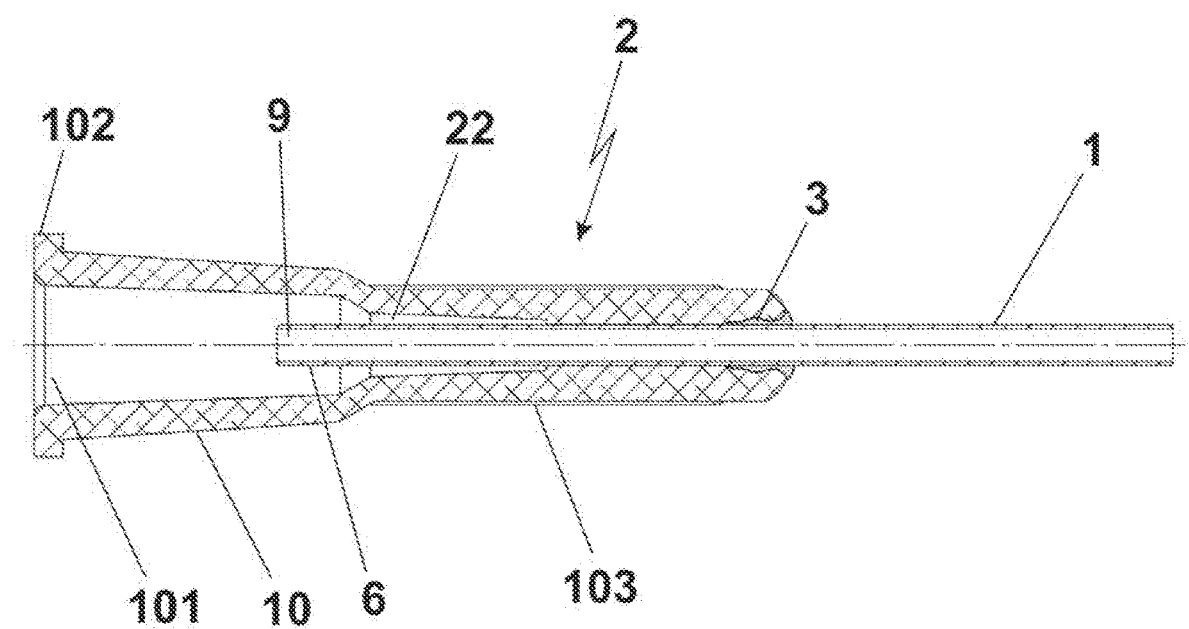

FIG. 7—a cross-sectional side view of the rear part of the second embodiment of the follicular needle.

According to FIGS. 1 to 5 as presented, the follicular aspiration needle, in the first embodiment, comprises a base part 2 with a through-hole, inside of which a needle cannula 1 is coupled. The needle cannula 1 has a front aspiration end 11 which protrudes from the front end of the base 2, and a rear end 9 which freely protrudes from the rear end of the base 2. Accordingly, a gap 6 is formed between the outer surface of the cannula 1 in the portion near to the rear end 9 and the inner surface of the base 2 in the region of the frustro-conical segment 22, near to the rear end of the base 2, such that it will be coupled in this space to the line 7 for collecting the biological sample of the follicular aspiration system, through which the biological sample passes, suctioned by a suction pump (not illustrated) coupled to the opposite end of the line 7.

At the rear end of the base 2 there is an opening 21 preferably greater in diameter than the through-hole, to facilitate introducing the line 7 and coupling thereof to the cannula 1. Subsequent to this opening 21, the through-hole has a frustro-conical segment 22 whose diameter decreases towards the front end of the base 2. For example, the diameter of this frustro-conical segment 22 varies from 2.01 mm at its larger end to 1.61 mm at the smaller opposite end. The end of the line 7 is coupled in this frustro-conical segment 22 of the base. The slant of this frustro-conical segment has a maximum angle of 15° in the axial direction, which will enable seal-tight coupling of the line 7 between the inner face of the base 2 and the outer periphery of the cannula 1.

When the line 7 is coupled to the base 2 of the needle, it is inserted into the space formed between the frustro-conical segment of the base 2 and the cannula 1, until the walls of the line 7 are pressed between the outer peripheral surface of the needle cannula 1 and the inner surface of the base 2, such that the line 7 is suitably sealed and fastened to the needle, and the use of an intermediary part is no longer necessary.

According to the present invention, the follicular aspiration cannula 1 may be constructed with an outer diameter of between 1 and 3 mm, and preferably about 1.61 mm, and these dimensions are smaller than those of the normal-standard cannulas used. The lesser diameter of the cannula enables the use of a line 7 also having a lesser diameter when compared to the standards normally used, with an inner diameter that may be from 1.8 to 1.9 mm and outer diameter of about 2.01 mm. Consequently, the aspiration guide device may also be constructed with lesser diameters than standard, causing less inconvenience to the animal. According to this embodiment of the invention, the opening 21 at the rear end of the base 2 may be constructed with a diameter of about 2.51 mm, which progressively decreases up to the frustro-conical segment 22. This larger-diameter opening 21 therefore provides for easy introduction of the line 7 inside the base 22, for coupling with the cannula.

Additionally, if necessary, in the embodiment of the invention according to FIGS. 1 to 5, the base 2 further comprises external threads 8 for improved fastening of a mandrill or elongated rod (not shown) to assist in coupling the line 7 on the needle, and a grip 12, which facilitates handling the needle. The threads 8 are disposed in the region of the base 2 corresponding to the frustro-conical segment 22, whereas the grip 12 is disposed in the opposite region, near to the front end of the cannula 1 and the base 2.

FIGS. 6 and 7 present a second embodiment of the follicular needle, wherein the base 2 comprises a grip region 103, a frustro-conical profile elongation 10 which extends from the rear portion of the base 2 and whose rear end has an edge in the shape of an annular ledge 102 and an opening 101 having a greater diameter than the remainder of the through-hole, to assist with fitting and coupling with the elongated rod. The opening 101 of the frustro-conical elongation 10 is adjacent to the frustro-conical segment 22 of the base 2. This opening 101 also has a frustro-conical profile whose diameter decreases towards the front end of the base 2, where the line 7 will be fastened and sealed. Depending on its diameter, the elongated rod may be externally coupled to the elongation 10 only in the region of the annular ledge 102, or else in a way that the remainder of the elongation is inserted into the end of the rod. Alternatively, if the rod has a smaller outer diameter than the elongation 10, it may be inserted into the opening 101, until it is firmly coupled inside the elongation 10, being pressed against the inner surface of the opening 101. Accordingly, the needle according to the present invention is compatible with various sizes of elongated rods, and may be coupled in a seal-tight and simple manner to any type of rod.

Using the follicular needle presented in the present invention has therefore been made easier, to the extent that to assemble the follicular aspiration system, it is suffice to connect the line 7 inside the frustro-conical segment 22 of the base 2.

The new follicular needle, thus conceived, offers the following advantages compared to its counterparts known to-date:
- ease and convenience of assembling the follicular needle in the aspiration system, since it is suffice to connect the line 7 directly at the base 2 of the needle;
- sealing guarantee, as the frustro-conical segment 22 having decreasing diameter towards the front end of the cannula 1 presses the walls of the line 7 against the outer surface of the needle cannula 1;
- easy fastening of the elongating rod or mandrill, by way of the threads 8 or the fitting 102 in the frustro-conical opening 101;
- the construction of the needle with few components firmly coupled enables the components used to have a lesser diameter compared to the standard aspiration devices available on the market, being less harmful to the animal at the moment of aspiration; and
- easy adaptation to different types of guide devices or elongated rods for aspiration devices.

Therefore, the scope of the present invention should not be limited to the details described herein, but rather solely to the terms defined in the claims and equivalents thereof.

The invention claimed is:

1. A needle for follicular aspiration, comprising:
   a base with a through-hole, inside of which a needle cannula is coupled, wherein the needle cannula has a front aspiration end which protrudes from a front end of the base, and where the needle cannula has a rear end which freely protrudes from a rear end of the base,
   the through-hole of the base has a frustro-conical segment tapering from the rear end towards the front end of the base, forming a gap between an inner surface of the base and an outer surface of the needle cannula for coupling a biological sample collecting line, and
   wherein the base comprises threads at the rear end.

2. The needle for follicular aspiration according to claim 1, wherein the base comprises a grip near the front end of the base.

3. The needle for follicular aspiration according to claim 2, wherein an outer diameter of the needle cannula is between about 1 and about 3 mm.

4. The needle for follicular aspiration according to claim 1, wherein a frustro-conical elongation extends from the rear end of the base, the frustro-conical elongation including an interior with a frustro-conical profile, and wherein a back end of the frustro-conical elongation includes an edge in the shape of an annular ledge for fastening.

5. The needle for follicular aspiration according to claim 4, wherein an outer diameter of the needle cannula is between 1 and 3 mm.

6. The needle for follicular aspiration according to claim 1, wherein an outer diameter of the needle cannula is between 1 and 3 mm.

7. The needle for follicular aspiration according to claim 6, wherein the frustro-conical segment has a maximum slant angle of 15°.

8. The needle for follicular aspiration according to claim 7, wherein an interior diameter of the frustro-conical segment decreases from 2.01 mm proximate to the rear end of the base to 1.61 mm proximate to the front end of the base.

9. The needle for follicular aspiration according to claim 1, wherein a biological sample collection line is coupled to the base in the gap between the inner surface of the base and the outer surface of the needle cannula; and
   wherein an inner diameter of the biological sample collection line is between 1.8 and 1.9 mm and an outer diameter of the biological sample collection line is at most about 2.01 mm.

10. A needle for follicular aspiration, comprising:
    a base with a through-hole, inside of which a needle cannula is coupled, wherein the needle cannula has a front aspiration end which protrudes from a front end of the base, and where the needle cannula has a rear end which freely protrudes from a rear end of the base;
    wherein the through-hole of the base has a frustro-conical segment tapering from the rear end towards the front end of the base, forming a gap between an inner surface of the base and an outer surface of the needle cannula for coupling a biological sample collecting line; and
    wherein a frustro-conical elongation extends from the rear end of the base, the frustro-conical elongation including an interior with a frustro-conical profile and a back end which includes an edge in the shape of an annular ledge for fastening.

11. The needle for follicular aspiration according to claim 10, wherein the base comprises a grip near the front end of the base.

12. The needle for follicular aspiration according to claim 10, wherein the rear end of the base comprises threads.

13. The needle for follicular aspiration according to claim 10,
wherein an outer diameter of the needle cannula is between 1 and 3 mm;
wherein the frustro-conical segment has a maximum slant angle of 15° ; and
wherein an interior diameter of the frustro-conical segment decreases from 2.01 mm proximate to the rear end of the base to 1.61 mm proximate to the front end of the base.

14. The needle for follicular aspiration according to claim 10, wherein the base comprises a grip near the front end of the base.

15. The needle for follicular aspiration according to claim 10, wherein an outer diameter of the needle cannula is between 1 and 3 mm.

16. A needle for follicular aspiration, comprising:
a base with a through-hole, inside of which a needle cannula is coupled, wherein the needle cannula has a front aspiration end which protrudes from a front end of the base, and where the needle cannula has a rear end which freely protrudes from a rear end of the base;
wherein the through-hole of the base has a frustro-conical segment tapering from the rear end towards the front end of the base, forming a gap between an inner surface of the base and an outer surface of the needle cannula for coupling a biological sample collecting line;
wherein an outer diameter of the needle cannula is between 1 to 3 mm;
wherein the frustro-conical segment has a maximum slant angle of 15°; and
wherein an interior diameter of the frustro-conical segment varies from 2.01 mm proximate to the rear end of the base to 1.61 mm proximate to the front end of the base.

17. The needle for follicular aspiration according to claim 16, wherein the rear end of the base comprises threads.

18. The needle for follicular aspiration according to claim 16, wherein a frustro-conical elongation extends from the rear end of the base, wherein the frustro-conical elongation includes an interior with a frustro-conical profile, and wherein a back end of the frustro-conical elongation includes an edge in the shape of an annular ledge for fastening.

19. The needle for follicular aspiration according to claim 16, wherein the base comprises a grip near the front end of the base.

* * * * *